United States Patent [19]

Wiegerinck

[11] Patent Number: 5,405,324
[45] Date of Patent: Apr. 11, 1995

[54] IMPLANTATION DEVICE

[75] Inventor: Maarten A. H. M. Wiegerinck, Eindhoven, Netherlands

[73] Assignee: Akzo N.V., Arnhem, Netherlands

[21] Appl. No.: 38,757

[22] Filed: Mar. 30, 1993

[30] Foreign Application Priority Data

Mar. 30, 1992 [NL] Netherlands ............. 9200581

[51] Int. Cl.6 ........................................... A61M 31/00
[52] U.S. Cl. .......................................... 604/60; 604/59; 128/754
[58] Field of Search ................... 604/60–64, 604/16, 18, 57–59, 132, 891.1, 274, 164, 48, 66, 272, 240; 128/749–755, 762; 606/167, 170, 171

[56] References Cited

U.S. PATENT DOCUMENTS 1,006,341 10/1911 Ammons ............................. 604/59
4,186,750 2/1980 Patel .................................. 128/748
4,356,828 11/1982 Jamshidi ............................ 128/754

OTHER PUBLICATIONS

Wiegerinck et al., "Experiences with a new needle-system for implantation of oestradiol," Medisch Journaal, vol. 21, No. 4, pp. 222–224, (1992).

Primary Examiner—C. Fred Rosenbaum
Assistant Examiner—V. Alexander
Attorney, Agent, or Firm—Mary E. Gormley

[57] ABSTRACT

The invention relates to an implantation device with which a medicinal implant can be introduced subcutaneously in humans or animals. The device comprises a hollow needle and a mandrel having a chamfered distal end, which precisely coincides with the plane of the chamfered distal end of the hollow needle. The invention also relates to a method for introducing an implant into subcutaneous tissue of humans or animals using the implantation device.

8 Claims, 2 Drawing Sheets

IMPLANTATION DEVICE

The invention relates to an implantation device with which a medicinal implant (small rod, pill, tablet, granule and the like which incorporates a pharmaceutically active substance) can be introduced subcutaneously in humans or animals or into subcutaneous tissue of humans or animals in an easy, effective and aseptic way.

The implanting of a pharmaceutical preparation subcutaneously or in subcutaneous tissue is normally used in human and veterinary medicine to achieve a long-term action of the pharmacon. The implant introduced (small rod, pill, tablet, granule, etc) slowly dissolves in the surrounding tissue or slowly releases the pharmacon thereto, and the pharmacon goes into circulation via the blood or the lymph in order then to be transported to the site or sites where it can perform its action. Thus, for example, in gynecology a tablet containing an oestrogen, for example oestradiol, is implanted in women after a double ovariectomy or in women during menopause in order to counteract or prevent certain symptoms from which these women suffer or may suffer. In animals implants which contain hormones are, for example, introduced subcutaneously in order to regulate oestrus.

A conventional method of subcutaneously introducing tablets containing an active substance is that in which a cut which measures approximately 5 mm is made in the skin with a small knife, after which a metal pin (trocar) in a cannula is pressed into the interior through the cut. After the trocar has been removed, the tablet is placed in the cannula from the top using sterile tweezers, after which the tablet is pushed into the cannula using an obturator and is forced out of the cannula into the subcutaneous tissue. (See, for example, Br. Med. J. 1980, i, 848–850.) Some of the drawbacks of this method are the possibility of haematoma formation due to piercing of blood vessels, the possibility of infection, the high resistance which is sometimes encountered in the subcutaneous tissue while pushing through the cannula, and the fact that a scar having cosmetic drawbacks is left behind.

Ned. Tijdschr. Geneesk. 1986; 130, No. 51; 2301–2303 discloses a so-called "rapid needle method" for subcutaneously implanting a tablet, in which method use is made of a hollow needle which is chamfered at the end, has an inside diameter of 3.0 mm and a length of 14 cm and which has a Luer-Lok at the lateral end. The tablet, (in the case described a cylindrical small rod which contains an oestradiol and has a diameter of 2.00–2.25 mm and a length of 4 to 5 mm) is placed by means of tweezers in the distal end of the hollow needle, that is to say at the chamfered sharp end. The disinfected and possibly locally anaesthetised skin is pierced with the "loaded" needle at an angle, after which a suitable bulbous probe having a length of 25 cm is introduced into the needle in order to push the tablet into the subcutaneous tissue therewith. The needle is then withdrawn along with the probe and the penetration point is covered with an absorbent gauze. Stitching is unnecessary and the perforation leaves virtually no scar behind. The drawback of this method is that some manipulation has still to be carried out with the loose components used in this method of implantation, viz. the needle, the tablet and the bulbous probe.

German patent 806,702 by Brune describes an implantation device having a hollow needle, mandrel, and a block-shaped part for introducing the implant. However, the mandrel of this device has an obtuse end and the block-shaped part is attached to the other side of the devise (i.e. at the other side of the top of the needle). The obtuse end of the mandrel has the disadvantage that this device leaves scars, whereas the attachment of the block-shaped part prevents that the device can be used in a manner as described in this invention.

The present invention provides an implantation device with which the abovementioned drawbacks can be eliminated. The device forms an integral whole and does not comprise loose components during use. In the device according to the invention, four parts are to be distinguished: a needle part, a handle part firmly joined to the needle part, an elongated part which can be pushed into the needle part and the handle part and with which the implant can be displaced, and a part incorporated in the handle part for feeding the implant into the proximal end of the needle part. The components of the device are made of a hard material, for example stainless steel. Certain parts of the device may also be made of a hard plastic, for example a hard type of PVC, certain nylons, PTFE, acrylates such as PPMA, polypropene, polystyrene, polycarbonate or polyoxymethylene, provided that the needle part and said elongated part, or at least the distal parts thereof, are always made of metal, preferably stainless steel.

The needle part comprises a hollow needle which is chamfered at the distal end, specifically in such a way that there is a sharp point with which the skin can be pierced, and is firmly joined at the proximal end to the handle part and merges without a junction into a tube part of the handle part or into a bore which is provided in the part serving to feed the implant in and which has the same inside diameter.

The handle part is thicker than the needle part and may be tubular, but it may also have a different cross section, as will be explained in still greater detail below. The handle part should, of course, have a shape such that the device can easily be handled for the purpose for which the device is intended. Thus, recesses can be provided in which the fingers, for example thumb and index finger, fit in order to enable the device to be held firmly during use. The handle part contains a cavity in the longitudinal direction which has a cross section which is equally as great as, or greater than, the inside diameter of the hollow needle.

The elongated part which can be pushed into the needle part and the handle part and with which the implant can be displaced into the needle comprises a solid small rod (also referred to as a mandrel) whose distal end is chamfered, specifically at precisely the same angle as the hollow needle. The mandrel has a length which is greater than the length of the hollow needle part and it expediently normally has a length which is approximately equal to the length of the hollow needle and the handle part together. The diameter of the mandrel is matched to the inside diameter of the hollow needle in such a way that the mandrel can easily be pushed to and fro in the needle, but without exhibiting more play than is absolutely necessary. The mandrel is pushed into the hollow needle in such a way that the chamfered end precisely coincides with the chamfered end of the hollow needle, as a result of which a solid needle is, as it were, produced. With the solid needle formed in this way, the skin and the subcutaneous tissue is pricked at the site where it is desired to introduce the implant, normally at an oblique angle. The advantage of using a chamfered solid needle is that the tissue is split and not punched. As a result, the tissue is damaged to a lesser extent and the healing of the prick proceeds more quickly, virtually without leaving any scar. With a hollow chamfered needle, there is a greater possibility in that some tissue will enter the needle as a result of the punching action, the tissue damage therefore becomes somewhat greater and the healing of the prick lasts somewhat longer, with a greater probability of some visible scar.

The part for feeding in the implant to the proximal end of the needle comprises a block-shaped part having a central bore which extends in the longitudinal direction therein, in which the proximal end of the needle is mounted and whose diameter is equal to the inside diameter of the needle. Provided in one side of said block-shaped part is a cup-shaped recess which extends down to the bore, all this being such that, between the bottom of the cup-shaped recess and the bore, there is an opening into which the implant fits, in the case of a rod-shaped implant (such as an implantation tablet which contains oestradiol and which is marketed under the brand name Dimenformon by N.V. Organon te Oss, The Netherlands), for example, an elongated opening in the longitudinal direction of the bore, and consequently of the needle, having dimensions of, for example, 5×2.5 mm. The block-shaped part may also serve as handle part. Recesses into which thumb and index finger fit neatly are provided on either side of the block-shaped part for the purpose of easily picking up and handling the device.

When the mandrel is pushed into the needle, the opening between the cup-shaped space and the bore (and, consequently, the needle) is closed off. Provisions have been made in order to ensure that, when the mandrel is fully pushed in, the chamfered needle point and the chamfered end of the mandrel coincide precisely. The skin and the subcutaneous tissue are pierced to the required depth with the then solid needle, after which the mandrel is withdrawn far enough to free the opening between the cup-shaped space and the bore (and, consequently, the hollow needle). Of course, desired provisions may also be made for this purpose. The implant is placed in the cup-shaped space using tweezers and, as a result of the shape of said space and of the opening in the bottom thereof, the implant enters the bore (and, consequently, the proximal end of the hollow needle) in the correct way. Instead of using tweezers, the implant may also be dropped into the cup-shaped space from a blister strip. The shape of the cup-shaped space then ensures that the implant enters the bore (and, consequently, the proximal end of the needle) correctly. The implant can now easily be pushed through the hollow needle into the subcutaneous tissue using the mandrel.

It should also be noted that the point of the chamfered needle, and consequently also the point of the chamfered mandrel, are situated in this case at the "top" of the device, that is to say at the side on which the cup-shaped space in the block-shaped part is situated. When the mandrel is withdrawn, the chamfered end thereof will then assume a beneficial position with respect to the implant, specifically in the sense that, as the implant is fed forward, it is pressed down in the bore and is thus conveyed more satisfactorily out of the bore in the hollow needle. After the implant has been fed forward, it ends up under the chamfered needle point when the mandrel is in the fully pushed-in position. When the needle is then withdrawn, this position of the needle point eliminates the risk of the implant being entrained on the needle point in the direction of the perforation.

Some embodiments of the device according to the invention will be described in detail below, with reference to the accompanying drawings. The embodiments described do not by any means have the intention of restricting the invention in any way.

FIG. 7 shows another embodiment of a device according to the invention in perspective, with the mandrel fully pushed in.

Figure 1:
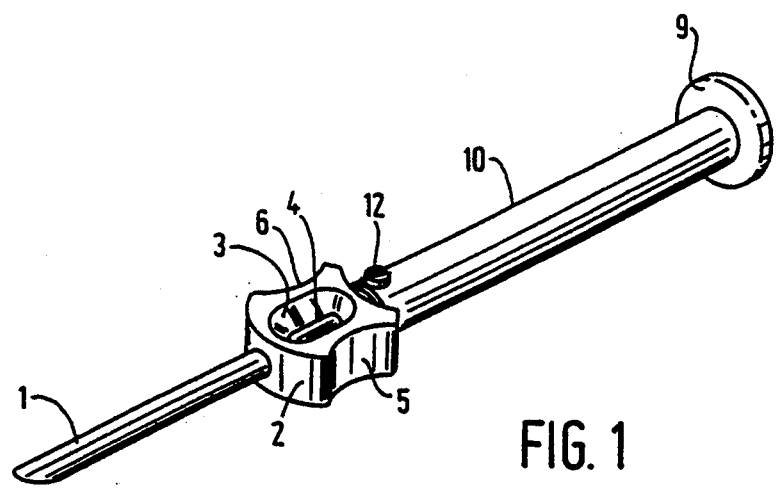
FIG. 1 shows an embodiment of a device according to the invention in perspective, the mandrel being pushed completely into the hollow needle.
Figure 2:
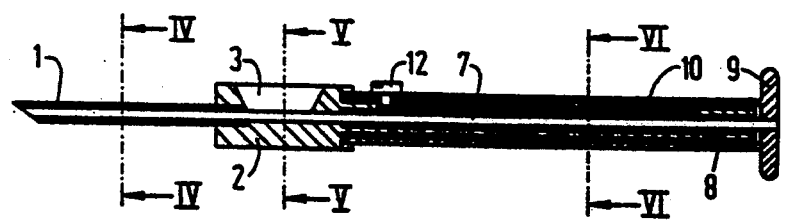
FIG. 2 shows a section in the longitudinal direction through the centre line of the device shown in FIG. 1.
Figure 3:
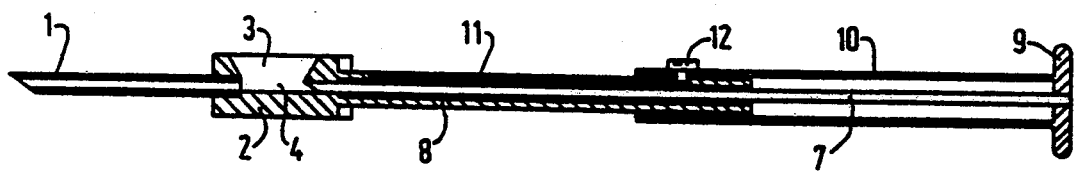
FIG. 3 shows a section in the longitudinal direction through the centre line of the device shown in FIG. 1, the mandrel being shown in the fully withdrawn position.
Figure 4:
FIG. 4 shows a cross section through the device along the line IV—IV in FIG. 2.
Figure 5:
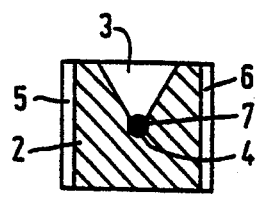
FIG. 5 shows a cross section through the device along the line V—V in FIG. 2.
Figure 6:
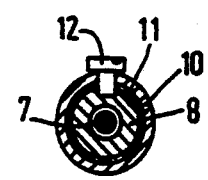
FIG. 6 shows a cross section through the device along the line VI—VI in FIG. 2.
Figure 7:
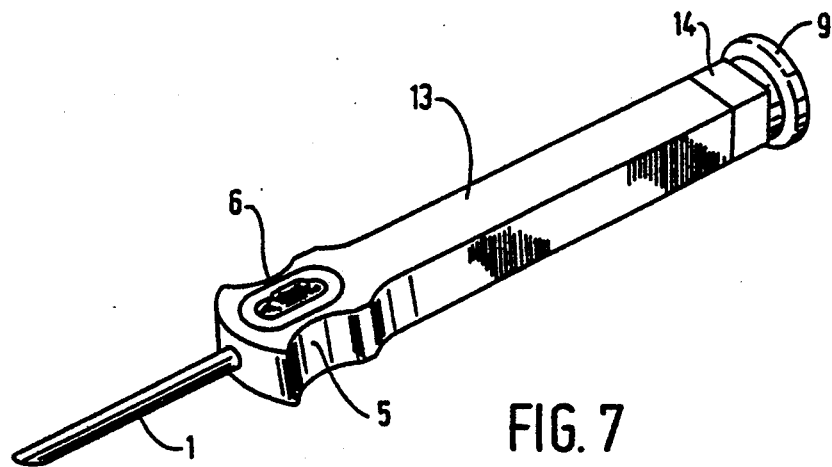
Figure 8:
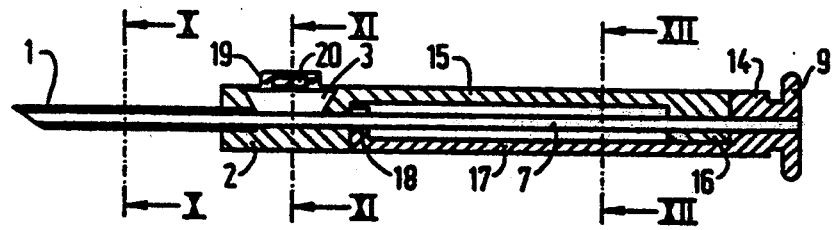
FIG. 8 shows a section in the longitudinal direction through the centre line of the device shown in FIG. 7.
Figure 9:
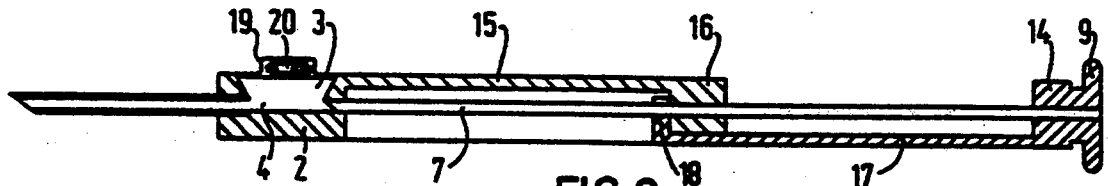
FIG. 9 shows a section in the longitudinal direction through the centre line of the device shown in FIG. 7, the mandrel being shown in the fully withdrawn position.
Figures 10, 11:
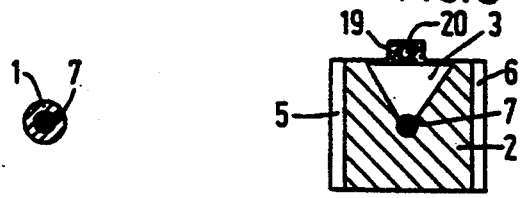
FIG. 10 shows a cross section through the device along the line X—X in FIG. 8.
FIG. 11 shows a cross section through the device along the line XI—XI in FIG. 8.
Figure 12:
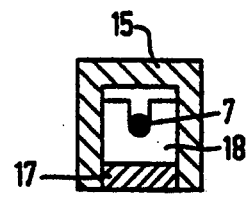
FIG. 12 shows a cross section through the device along the line XII—XII in FIG. 8.

The device shown in FIGS. 1-6 comprises a hollow needle 1 which is chamfered at the distal end and has an inside diameter of 2.5 mm and whose proximal end is mounted in a block 2 in a way which can be clearly seen in FIGS. 2 and 3. Block 2 comprises an elongate, cup-shaped cavity 3 extending from the top and having an elongate opening in the bottom of said cavity which gives access to a bore 4 provided in the block 2 in line with the needle 1 and having the same diameter as the inside diameter of the needle 1. The dimensions of the opening in the bottom of the cavity 3 match those of an implant to be introduced in such a way that the implant can easily be placed in the bore via said opening, specifically by placing the implant in the cavity 3 using tweezers or by allowing it to drop. The shape of the cavity 3 contributes to the fact that the implant enters the bore in the correct position.

Provided at the sides of the block 2 are recesses 5 and 6 into which thumb and index finger fit so that the device can be grasped firmly. That side of the block 2 gripping the needle which faces the body during use preferably has a rounded shape, as is clearly shown in FIG. 1.

Situated in the hollow needle 1 is the front part of a mandrel 7 having a chamfered distal end which, in this position, precisely coincides with the plane of the chamfered distal end of the hollow needle 1 (see FIGS. 1 and 2). From the front part, the mandrel 7 extends rearwards through the bore into the block 2 and then through a tubular member 8 (in this embodiment a round tube, but other sections, for example rectangular, are also possible) which is situated behind the block 2 and is attached to said block and which has a length which is at least equal to the length of the needle 1 and the block 2 together. The inside diameter of the tube 8 is equal to that of the hollow needle 1 and the bore 4, so that there is a central channel of equal diameter over the entire length of the device, the diameter of the mandrel 7 being such that it in fact completely fills the channel but can easily be moved to and fro therein in a sliding manner. Attached to the proximal end of the mandrel 7, which projects somewhat outside the tube 8 in the completely pushed-forward position of the mandrel 7, is a disc 9 with which the mandrel 7 can easily be manipulated. In the fully pushed-forward position of the mandrel 7 the disc 9 abuts against the face of the proximal end of the tube 8. Attached to the disc 9, moreover, is also a tubular member 10 (in this embodiment also a round tube) that is situated around tube 8 and has an inside diameter such that it fits closely and in a sliding manner around the latter. The length of the tube 10 is approximately equal to the length of the tube 8. Provided in the outside circumference of the tube 8 in the longitudinal direction is a groove 11 in which a protrusion 12 provided on the inside of the tube 10 slides. Such a protrusion 12 can easily be formed by providing a threaded hole in the tube 10 and screwing a screw into it until it projects inwards to such an extent that it precisely fits into the groove 11. The length of the groove 11 is, on the one hand, such that the protrusion or screw 12 abuts against the distal end of the groove when the mandrel 7 is pushed forward at the instant when the chamfered end of the needle 1 and the mandrel 7 coincide precisely, so that, in this way, the formation of a solid needle is ensured when the mandrel 7 is in the fully pushed-forward position and it is, on the other hand, such that, when the mandrel 7 is pushed backwards, the protrusion or screw 12 abuts against the proximal end of the groove at the instant when the distal point of the mandrel is situated just beyond the opening in the bottom of the cup-shaped cavity 3 in the block 2, so that the bore 4 in the block 2 is freed in order to be able to place the implant therein. If the screw 12 is removed, the mandrel 7, together with disc 9 and tube 10, can be removed from the device, and this has advantages when sterilising the device.

The device according to the invention in the embodiment of FIGS. 1–6 is preferably made completely of stainless steel. Stainless steel has the advantage that the device can easily be sterilised and the device can therefore always be reused. If it is desired to treat the device in this embodiment as a disposable device, certain components of the device may be constructed of a hard plastic from the point of view of cost, with the exception of the hollow needle 1 and the mandrel 7.

A device according to the invention in the embodiment as shown in FIGS. 7–12 is intended as a disposable device. In this embodiment, the hollow stainless-steel needle 1 is clamped at the proximal end in a holder 13 made of hard plastic.

In the holder 13, the same functional components are in fact to be distinguished as in the embodiment shown in FIGS. 1–6. The front part 2 of the holder 13 corresponds to the block 2 in FIGS. 1–6 and comprises the cup-shaped cavity 3 having an opening in the bottom thereof which gives access to the bore 4 which is in line with the hollow needle 1 and has the same diameter. On either side of said front part 2 are recesses 5 and 6 to enable the device to be held firmly. The mandrel 7, preferably made of stainless steel, is matched in terms of diameter to the inside diameter of the hollow needle 1 and the bore 4, and it is chamfered at the distal end in such a way that said end coincides precisely in the pushed-forward position with the plane of the chamfered end of the needle 1, so that mandrel and hollow needle together form a solid needle in this position. The proximal end of the mandrel 7 is clamped in a hard-plastic block 14, whose extreme end is formed as a disc 9 for the purpose of easily picking it up, as can clearly be seen in FIGS. 7–9. The round tubes 8 and 10 in the embodiment shown in FIGS. 1–6 are replaced in this embodiment by two block-shaped plastic components, of which one component 15 forms part of the holder 13 and of which the other component 17 is firmly joined to the block 14.

The block 15 is elongate in shape and is firmly joined by means of one end to the upper part of block 2, the top edges of the blocks 2 and 15 being in line with one another. Formed downwards at an angle of 90° at the other end of block 15 is a block-shaped projection 16 in which a bore is provided which is precisely in line with the bore 4 and has the same diameter. A mandrel 7 clamped in the block 14 runs through the bore in the projection 16 and is fixed in this way in the transverse direction with respect to the device.

The block 17 is also elongated in shape and is firmly joined by means of one end to the bottom part of block 14, the lower edges of the blocks 14 and 17 being in line with one another. Formed at an angle of 90° at the other end of block 17 is a projection 18 through which the mandrel 7 projects and by which the extreme positions of the mandrel in the device are determined. The dimensions of the blocks 15 and 16, on the one hand, and those of the blocks 17 and 18, on the other hand, are matched to one another in the longitudinal direction of the device in such a way that the chamfered end of the mandrel 7 coincides precisely in the fully pushed-in position thereof with the plane of the chamfered end of the hollow needle 1 (see FIG. 8) and is situated in the fully withdrawn position just past the opening between the bottom of the cup-shaped space 3 and the bore 4 (see FIG. 9).

In the embodiment of a device according to the invention shown in FIGS. 7–12, a special design of the feed of the implant is indicated. The implant 20, in this case a rod-shaped tablet having a diameter of 2.15 mm and a length of 4 mm, is packaged in a sterile manner in a blister strip 19 whose dimensions are such that the strip is somewhat larger than the opening at the top of the cup-shaped space 3. The strip 19 can then be laid on said opening when the device is in use or is firmly glued beforehand around said opening by its circumferential edge. When the device is in use, the blister strip 19 can be pressed in at the instant when the mandrel is set to the fully withdrawn position, as a result of which the implant 20 drops out of the strip into the cup-shaped space 3 and, via said space, ends up in the correct position in the bore 4. The implant 20 can then be placed in the subcutaneous tissue by means of the needle 1 by pushing the mandrel fully in. The supply of the implant by means of a blister strip glued to the device beforehand still more satisfactorily ensures a sterile feed of the implant. Of course, the distance of the bottom membrane of the blister strip from the bore 4, in other words the depth of the cup-shaped space, is such that the tear edges of the bottom membrane remain inside the cup-shaped space after said membrane has been torn (that is to say after the implant has been pressed through). This ensures that no part of the bottom membrane is unintentionally carried through into the hollow needle 1 by the mandrel 7.

It will be clear that, within the scope of the invention, the implantation device may also take forms other than those described above and this certainly applies to certain components of the device according to the invention such as the handle part and those components which determine the extreme positions of the mandrel.

For the sake of completeness, the procedures during the use of the device according to the invention will be described below.

At the site where it is desired to introduce the implant subcutaneously, the skin is sterilised in the normal manner, after which local anaesthetization is carried out, for example by injecting a local anaesthetic such as lidocaine, and then the skin is pierced at an angle using the device, the mandrel being fully pushed in and the piercing is therefore done with a solid needle. During this oblique piercing, the device is handled with the sharp point downwards, that is to say it is, as it were, used upside down, as a result of which the piercing proceeds more easily. When the correct depth in the subcutaneous tissue has been reached, the device is rotated through 180°, so that the chamfered face formed by the needle and the pushed-in mandrel is then directed downwards. The mandrel is then fully withdrawn so that its point ends up beyond the feed opening for the implant. The implant is then introduced into the cup-shaped space (either from a sterile packaging using sterile tweezers, or from a sterile packaging with thumb and index finger inserted in sterile gloves, or from a blister strip provided on the device above the cup-shaped space) and, via the opening in the bottom of said space, into the bore and, consequently, into the proximal end of the hollow needle. The mandrel is then pushed in, its sharp point contributing to the fact that the implant is pressed down in the open portion of the bore. The implant is carried forward through the hollow needle by means of the mandrel into the subcutaneous tissue, after which the needle, together with the mandrel, is quickly withdrawn. A good deposition of the implant is promoted by the position of the chamfered end of the device (directed downwards) and the elasticity of the tissue cleaved during the piercing, the subcutaneous tissue and the skin virtually closing completely above the implant and the probability of expulsion being negligible. The prick does not have to be stitched; a small protective plaster (sterile strip) is sufficient.

Although a few things have been mentioned above in relation to the relative dimensions of the various components of the device according to the invention, it may also be noted with regard to the dimensions that, to use the implantation device for humans and small (domestic) animals the needle part normally has a length of 2–5 cm and the handle part, comprising the block having the cup-shaped space for feeding in the implant and the extension thereof for guiding the mandrel, normally has a length of 10–12 cm. With the mandrel in the fully pushed-in position, the complete device normally has a length of approximately 15 cm. For use with larger animals, for example agricultural animals, the device may be of larger construction, but the relative dimensions of the various components will remain approximately the same.

The device according to the invention makes a smooth, accurate and simple procedure possible for the subcutaneous introduction of an implant in humans or animals. No incision and no subsequent stitching are necessary. No expulsion takes place. The number of operations to be performed is a minimum. The placing of the implant in the hollow needle is considerably simplified compared with the known techniques. The mandrel does not have to be removed from the device and, in addition to the forward-feed function, it has the function of forming, by means of the chamfered distal end, a sharp solid needle together with the chamfered hollow needle in the pushed-in state and the function, after being fully withdrawn, of holding the implant in the correct position in the needle lumen during the forward feeding of the implant thereafter.

I claim:

1. An implant device comprising:
   a) a hollow needle part having a chamfered distal end to pierce skin;
   b) a handle part firmly joined to the hollow needle part;
   c) an elongated part which is movably displaced in the device, whereby an implant is movably displaced in the device; and
   d) a block-shaped part between the hollow needle part and the handle part, for feeding the implant into the hollow needle part and in which, starting from one side, a cup-shaped cavity is situated that extends almost halfway through the thickness of the block-shaped part, opening at a bottom side into a bore in the block-shaped part, said bore being in line with the hollow needle part and having the same diameter as the inside diameter of the hollow needle part, an opening between the cup-shaped cavity and the bore being large enough to enable the implant to be introduced into the bore and then into the proximal end of the hollow needle part; and wherein
   e) the elongated part that is movably displaced in the device comprises a mandrel whose distal end is chamfered at the same angle as the distal end of the hollow needle part, said mandrel being approximately equal to the length of said hollow needle part, said block-shaped part and said handle part together; and the diameter of said mandrel being matched to the inside diameter of the hollow needle part so that the mandrel can easily be pushed forward and backward, but as a close fit in the hollow needle part and in the bore of the block-shaped part, wherein the chamfered end of the mandrel coincides precisely with the plane of the chamfered end of the hollow needle part in the fully push-in position thereof, while also freeing the opening between the cup-shaped cavity and the bore in the block-shaped part that serves to feed in the implant in the fully withdrawn position of the mandrel.

2. A device according to claim 1, wherein said block-shaped part that serves to feed in the implant also serves as a handle part or forms a component thereof.

3. A device according to claim 1, wherein the chamfered end of the mandrel and the plane of the chamfered end of the hollow needle are made to coincide precisely in the pushed-in position while freeing the feed opening for the implant in the withdrawn position of the mandrel by the device comprising:

a) a first tubular member which is attached to the block-shaped part in line with the hollow needle part and said bore and whose inside diameter is equal to that of the hollow needle part and the bore, so that a channel is produced in the device into which the mandrel can be pushed to and fro in a close fit;

b) a second tubular member which is a close fit, but displaceably around the first tubular member and that is attached to the proximal end of the mandrel; and c) a groove on the outside of the first tubular member in the longitudinal direction thereof and a protrusion which fits into said groove being provided on the inside of the second tubular member, and the length of the groove being such that, at the extreme positions of the protrusion in the groove, said desired positions of the mandrel are reached.

4. A device according to claim 1, wherein the chamfered end of the mandrel and the plane of the chamfered end of the hollow needle part coincide precisely in the pushed-in position while freeing the feed opening for the implant in the withdrawn position of the mandrel by the device comprising:

(1) an elongated block which is fixed on the block-shaped part above the bore thereof and extends backwards, a projection being formed downwards at an angle of 90° at the rear side of said elongated block, in which projection a bore is provided which is situated precisely in line with the bore in the block-shaped part and has the same diameter and through which the mandrel extends, and (2) a block attached to the proximal end of the mandrel with an elongated block fixed underneath the mandrel and extending forward, a projection being formed upwards at an angle of 90° at the front of said elongated block, through which projection the mandrel projects and is firmly joined thereto, and said upwardly formed projection abutting against the block-shaped part having the cup-shaped cavity with the mandrel completely pushed in and abutting against said downwardly formed projection with the mandrel fully withdrawn.

5. A device according to claim 1 wherein a sharp point of the chamfered needle part, and consequently also a sharp point of the chamfered distal end of the mandrel, are situated on that side of the device where the cup-shaped cavity is situated.

6. A device according to claim 1, wherein apart from the hollow needle part and the mandrel, the device is constructed from a hard plastic.

7. A device according to claim 1, wherein the cup-shaped cavity is closed off at the top by a blister strip in which the implant is situated and whose blister membrane is directed towards the cup-shaped cavity.

8. A method of introducing an implant into subcutaneous tissue of human or animals, comprising piercing the skin or tissue of the humans or animals with an implant device comprising:

a) a hollow needle part having a chamfered distal end to pierce skin;

b) a handle part firmly joined to the hollow needle part;

c) an elongated part which is movably displaced in the device, whereby an implant is movably displaced in the device; and d) a block-shaped part between the hollow needle part and the handle part, for feeding the implant into the hollow needle part and in which, starting from one side, a cup-shaped cavity is situated that extends almost halfway through the thickness of the block-shaped part, opening at a bottom side into a bore in the block-shaped part, said bore being in line with the hollow needle part and having the same diameter as the inside diameter of the hollow needle part, an opening between the cup-shaped cavity and the bore being large enough to enable the implant to be introduced into the bore and then into the proximal end of the hollow needle part; and wherein e) the elongated part that is movably displaced in the device comprises a mandrel whose distal end is chamfered at the same angle as the distal end of the hollow needle part, said mandrel being approximately equal to the length of said hollow needle part, said block-shaped part and said handle part together; and the diameter of said mandrel being matched to the inside diameter of the hollow needle part so that the mandrel can easily be pushed forward and backward, but as a close fit in the hollow needle part and in the bore of the block-shaped part, wherein the chamfered end of the mandrel coincides precisely with the plane of the chamfered end of the hollow needle part in the fully push-in position thereof, while also freeing the opening between the cup-shaped cavity and the bore in the block-shaped part that serves to feed in the implant in the fully withdrawn position of the mandrel, fully pushing in the mandrel such that the needle is made solid, with the device being held in a position that the sharp point and the blocked-shaped part points downwards; rotating the device through approximately 180°; withdrawing the mandrel so that its point is beyond the feed opening for the implant; introducing the implant into the device through block-shaped part; pushing the mandrel in; and ejecting the implant from the device into the subcutaneous space.

* * * * *